(12) United States Patent
Sanabria

(10) Patent No.: US 8,377,449 B2
(45) Date of Patent: Feb. 19, 2013

(54) FIVE PART HERBAL CLEANSE PROTOCOL (DETOXIFYING TEA, TONIFYING TEA, RELAXING TEA, PARASITE TEA, INTESTINAL TEA) IN CONJUNCTION WITH YOGA AND A VEGAN ALKALINIZING FOOD AND JUICE CLEANSE PROGRAM

(76) Inventor: Tatianna Sanabria, Cary, NC (US)

( * ) Notice: Subject to any disclaimer, the term of this patent is extended or adjusted under 35 U.S.C. 154(b) by 202 days.

(21) Appl. No.: 12/931,612

(22) Filed: Feb. 7, 2011

(65) Prior Publication Data

US 2012/0201909 A1    Aug. 9, 2012

(51) Int. Cl.
| | |
|---|---|
| *A61K 36/074* | (2006.01) |
| *A61K 36/53* | (2006.01) |
| *A61K 36/481* | (2006.01) |
| *A61K 36/815* | (2006.01) |
| *A61K 36/718* | (2006.01) |
| *A61K 36/804* | (2006.01) |
| *A61K 36/704* | (2006.01) |
| *A61K 36/25* | (2006.01) |
| *A61K 36/882* | (2006.01) |
| *A61K 36/725* | (2006.01) |
| *A61K 36/736* | (2006.01) |
| *A61K 36/67* | (2006.01) |

(52) U.S. Cl. ............... 424/195.15; 424/728; 424/756; 424/747; 424/744; 424/736; 424/764; 424/755; 424/735; 424/734; 424/765; 424/769; 424/773; 424/774; 424/775; 424/776; 424/777; 424/725

(58) Field of Classification Search ................... None
See application file for complete search history.

(56) References Cited

U.S. PATENT DOCUMENTS 6,790,464 B2 *   9/2004   Kuok et al. .................. 424/725

* cited by examiner

*Primary Examiner* — Susan Hoffman

(57) ABSTRACT

An herbal cleanse formulation comprising five different herbal teas: a parasite tea, an intestinal tea, a detoxifying tea, a tonifying tea, and a relaxing tea. The parasite tea comprises *areca* seed, black plum, Sichuan pepper, and daikon radish. The intestinal tea comprises mountain hawthorn berry, *magnolia* bark, *senna* leaf, *aloe*, *prunus*, bitter orange, rhubarb, and licorice. The detoxifying tea comprises *cyperus*, Chinese *angelica*, *trichosanthes*, honeysuckle, *forsythia*, burdock fruit, dandelion, *gardenia*, *coptis*, and mustard seed. The tonifying tea comprises goji berries, red reishi, *rehmannia, polygonum, astragalus*, ginseng, *codonopsis*, and *schizandra*. The relaxing tea comprises ginger, lily bulbs, *mimosa* tree bark, acorus, sour jujube seeds, yuan zhi, and mint. The herbal cleanse formulation are to be taken at specific times of the day for a determined number of days in a specific protocol in conjunction with a vegan alkalinizing diet and incorporating Kundalini yoga.

40 Claims, No Drawings

FIVE PART HERBAL CLEANSE PROTOCOL (DETOXIFYING TEA, TONIFYING TEA, RELAXING TEA, PARASITE TEA, INTESTINAL TEA) IN CONJUNCTION WITH YOGA AND A VEGAN ALKALINIZING FOOD AND JUICE CLEANSE PROGRAM

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC APPENDIX

Not Applicable

BACKGROUND OF THE INVENTION

Herbal cleanse formulations can provide a natural way to eliminate toxins and congestion that builds up in your body. Such formulations are useful in eliminating parasites, promoting the healthy function of the intestines, cleaning the body of toxins, allowing a free flow of energy, tonifying and nourishing the body, slowing the aging process and calming and relaxing the body.

Parasites are organisms that live inside a living being. They cannot survive without a host. They can inhabit any living creature. Parasites are harmful to our bodies and their waste is toxic and causes sickness and disease, if not properly treated. Parasites can be transferred from blood sucking insects and mosquitoes, from pets to owners and from person to person, or if hands are not washed after using the bathroom and then food is prepared.

Intestinal parasites are parasites that populate the gastrointestinal tract in humans and other animals. They can live throughout the body, but most prefer the intestinal wall. Means of exposure include: ingestion of undercooked meat, drinking infected water, and skin absorption.

All of us have intestinal parasites of the microscopic level living in our intestines. But there are certain intestinal parasites that are going to cause harmful or unwanted symptoms and therefore need to be removed. Intestinal parasites are normally removed by the body, which has its own natural detoxifying capabilities. Sometimes, such as when your immune system is low, your body is not able to deal with the intestinal parasites as well as it should.

The most noticeable symptoms of intestinal parasites are diarrhea, nausea, and perianal (itching of the outer anal area) itching. Some people may experience symptoms such as a runny nose, restlessness, or blisters upon the mouth. Others have experienced allergy type symptoms (sneezing, itching), headaches, increased appetite, and extreme fatigue. Other symptoms may include joint pain, chronic fatigue, and auto immune deficiencies (such as continually getting sick). If the parasites go untreated, a person can experience bad smelling stools, diarrhea, flu-like symptoms, loss of appetite, abdominal cramps and gas, mucous and blood in their stools, rashes and itching, and even passing worms in the stool. Intestinal parasites can cause intestinal obstruction and block necessary nutrients. People can also suffer with mental capacity and intestinal bleeding.

Constipation is infrequent bowel movements (typically three times or fewer per week), difficulty during defecation (straining during more than 25% of the bowel movements or a subjective sensation of hard stools), or the sensation of incomplete bowel evacuation.

Constipation is a symptom with many causes. These causes are of two types: obstructed defecation and colonic slow transit (or hypomobility). Causes of colonic slow transit constipation include diet, hormones, side effects of medications, and heavy metal toxicity. One of the main problems of constipation is the pain. Straining during bowel movements due to constipation may cause many issues. Hemorrhoids may develop, as can anal fissures, and rectal bleeding. Rectal prolapse, though rare, may occur, a condition where a piece of intestinal lining pushes from the anal opening. Constipation may also result in stool packing the intestine so tightly that it cannot be expelled, resulting in a condition called fecal impaction.

The colon is a breeding ground for both good and bad bacteria. When too much fermentation and putrefaction is produced in the colon by neglecting to keep it in good condition, it is necessary for the waste to be expelled from the body. And that is exactly why the colon is well-equipped with a very efficient system of elimination. But there is a big "if" here—the colon only does what it needs to do if it is in good working order. In a healthy colon environment, the good bacteria will control the bad. But in an unhealthy environment, the bad bacteria rule.

Constipation is unhealthy because toxins are formed and absorbed when waste remains in the intestines. If we don't eliminate toxins through our bowels properly, they will just sit in our body, allowing toxins to seep back into the blood stream, increasing the toxic load of the body.

Symptoms of constipation include pain, swollen abdomen or abdominal pain, and infrequent or difficulty in eliminating. Constipation can aggravate such issues as high cholesterol, obesity, diabetes, and weight gain.

The word toxic means all things that may do harm to the body. Toxins can show up in a variety of ways such as fever, sweats, swollen and sore throat, mumps, thirst, dysentery, diarrhea, carbuncles, boils, skin eruption and rashes, restlessness, insomnia, delirium, bleeding, subcutaneous and mucosa hemorrhage, auto immune diseases, allergies, infections, common colds, influenza, arthritis, high blood pressure and cholesterol, diabetes, ulcers, cirrhosis and jaundice, bladder infection, cancer, and more.

Detoxification is performed by a number of organs, glands, and transportation systems, including the skin, gut, kidneys, liver, lungs, lymphatic system, and mucous membranes.

Malnutrition is the condition that results from having an unbalances diet in which certain nutrients are lacking, are in excess, or in the wrong proportions. Without proper nutrition the body cannot function properly. A number of different nutrition disorders may arise, depending on which nutrients are under or overabundant in the diet. These disorders include anemia, goiter, hypothyroidism, osteoporosis, obesity, cardiovascular disease, hypertension, diabetes, nervous disorders and cancers to name a few.

A person may experience malnutrition in the form of fatigue, poor appetite, loose stool, bloating in the abdomen or epigastrium, shortness of breath, low voice, spontaneous sweating, palpitations, dribbling urine, frequent urination, incontinence, loose stool, weakness in the lumbar region and knee, sallow face, pale face, pale lips, pale tongue, pale nails, dizziness, insomnia, scanty menstruation or postdated-menstruation or amenorrhea, cold limbs, intolerance to cold, impotence, infertility, listlessness, and more.

Tension is a state of mental or emotional strain. Stress refers to the consequence of the failure of an organism to respond appropriately to emotional or physical threats, whether actual or imagined.

The human body is designed to experience stress and react to it. Stress can be positive, keeping us alert and ready to avoid danger. Stress becomes negative when a person faces continuous challenges without relief or relaxation between challenges. As a result, the person becomes overworked and stress-related tension builds.

Stress that continues without relief can lead to a condition called distress—a negative stress reaction. Distress can lead to physical symptoms including headaches, upset stomach, elevated blood pressure, chest pain, and problems sleeping. Research suggests that stress also can bring on or worsen certain symptoms or diseases. Stress symptoms commonly include a state of alarm and adrenaline production, short-term resistance as a coping mechanism, and exhaustion, as well as irritability, muscular tension, inability to concentrate and a variety of physiological reactions such as headache and elevated heart rate.

The autonomic nervous system provides the rapid response to stress commonly known as the fight-or-flight response, engaging the sympathetic nervous system and withdrawing the parasympathetic nervous system thereby enacting cardiovascular, respiratory, gastrointestinal, renal, and endocrine changes. Chronic stress can significantly affect many of the body's immune systems, as can an individual's perceptions of, and reaction to, stress. The term psychoneuroimmunology is used to describe the interactions between the mental state, nervous and immune systems, as well as research on the interconnections of these systems. Immune system changes can create more vulnerability to infection. Responses to stress include adaptation, psychological coping such as stress management, anxiety, and depression. Over the long term, distress can lead to diminished health and/or increased propensity to illness; to avoid this, stress must be managed.

Symptoms of tension can include anxiety, restlessness, irritability, depression, melancholy, stress, overworked mind, fidgeting, constrained emotions, dream-disturbed sleep, excessive brooding, fear, forgetfulness or poor memory, mental disorientation or confusion, neurasthenia, pent-up emotional states, palpitations, insomnia, spasm, and pain.

It would be desirable to prepare an herbal cleanse formulation protocol which would act to eliminate parasites, promote healthy function of the intestines, clean the body of toxins, allow a free flow of energy, tonify and nourish the body, slow the aging process and calm and relax the body.

BRIEF SUMMARY OF THE INVENTION

Accordant with the present invention, there has been discovered an herbal cleanse formulation protocol which is useful for eliminating parasites, promoting healthy function of the intestines, cleaning the body of toxins, creating a free flow of energy, tonifying and nourishing the body, slowing the aging process, and calming and relaxing the body. The herbal cleanse formulation comprises five separate herbal formulations which are to be taken at specific times of the day for a determined number of consecutive days in a specific protocol integrating kundalini yoga, and a vegan alkalinizing food and juice diet.

The five herbal formulations are comprised of: *areca* seed; black plum; Sichuan pepper; daikon radish; mountain hawthorn berry; *magnolia* bark; *senna* leaf; *aloe; prunus*; bitter orange; rhubarb; licorice; *cyperus;* Chinese *angelica; trichosanthes;* honeysuckle; *forsythia;* burdock fruit; dandelion; *gardenia; coptis;* mustard seed; goji berries; red reishi; *rehmannia; polygonum; astragalus; ginseng;* codonopsis; *schizandra;* ginger; lily bulbs; *mimosa* tree bark; acorns; sour jujube seeds; yuan zhi; and mint.

The herbal cleanse formulation protocol of the present invention is useful for cleaning toxins and congestion, eliminating parasites, promoting healthy function of the intestine, creating a free flow of energy, tonifying and nourishing the body, slowing the aging process, and calming and relaxing the body.

DETAILED DESCRIPTION OF THE INVENTION

The present invention is directed to an herbal cleanse formulation taken in a specific protocol in conjunction with a vegan alkalinizing diet and incorporating Kundalini yoga, and which is useful for eliminating parasites, promoting healthy function of the intestines, cleaning the body of toxins, creating a free flow of energy, tonifying and nourishing the body, slowing the aging process, and calming and relaxing the body. The herbal cleanse formulation comprises five different herbal teas: a parasite tea, an intestinal tea, a detoxifying tea, a tonifying tea, and a relaxing tea. The five herbal tea formulations are comprised of: *areca* seed; black plum; Sichuan pepper; daikon radish; mountain hawthorn berry; *magnolia* bark; *senna* leaf; *aloe; prunus;* bitter orange; rhubarb; licorice; *cyperus;* Chinese *angelica; trichosanthes;* honeysuckle; *forsythia;* burdock fruit; dandelion; *gardenia; coptis;* mustard seed; goji berries; red reishi; *rehmannia; polygonum; astragalus;* ginseng; codonopsis; *schizandra;* ginger; lily bulbs; *mimosa* tree bark; acorns; sour jujube seeds; yuan zhi; and mint. The teas are to be taken orally with hot water in specific dosages and at specific times of the day for a determined number of consecutive days, in conjunction with a diet of vegan alkalinizing food and juices in order to restore overall health and incorporating Kundalini yoga practiced under the supervision of a facilitator as part of the cleanse.

The herbal cleanse tea formulations are dispensed as granules designed to be mixed in specific dosages in about 8 ounces of hot water and taken orally at specific times of the day.

The parasite herbal tea formulation is useful in the elimination of parasites, including, but not limited to, asacariasis (roundworms), taeniasis (tapeworms), oxyuriasis (pinworms), and ancylostoma (hookworms). The parasite herbal tea comprises areca seed, black plum, Sichuan pepper and daikon radish. Six grams of the parasite herbal tea are to be mixed in about 8 ounces of hot water and taken orally first thing in the morning for a determined number of consecutive days. The recited ingredients are well-known medicinal Chinese herbs.

*Areca* seed, present in the parasite tea, expels and kills many kinds of intestinal parasites including tapeworms, hookworms, pinworms, and roundworms. It also has a laxative effect to excrete parasites from the intestines. In addition it treats food retention, abdominal distention and water retention. *Areca* seed comprises about 43 weight percent of the parasite tea.

Black plum, present in the parasite tea, is traditionally used to expel parasites, and is also used to treat roundworm and hookworm infection. Black plum comprises about 21 weight percent of the parasite tea.

Sichuan pepper, present in the parasite tea, expels parasites, kills round worms, is a natural pain reliever, boosts immunity and helps with weight loss. Sichuan pepper comprises about 21 weight percent of the parasite tea.

Daikon radish, present in the parasite tea, eliminates food retention, descends qi, and is often used as a digestive aid. Daikon radish comprises about 14 weight percent of the parasite tea.

The intestinal herbal tea formulation is useful in promoting healthy function of intestines and facilitating elimination. The intestinal tea formulation comprises mountain hawthorne berry, *magnolia* bark, *senna* leaf, exude from the leaves of *Aloe*, *prunus*, bitter orange, rhubarb and licorice. Five grams of the intestinal herbal tea are to be mixed in about 8 ounces of hot water and taken orally first thing in the morning right after the parasite tea formulation for a determined number of consecutive days. The recited ingredients are well-known medicinal Chinese herbs.

Mountain hawthorne berry, present in the intestinal tea, is one of the most popular herbs to aid digestion and eliminate food retention. It also lowers cholesterol. Mountain Hawthorne comprises about 20 weight percent of the intestinal tea.

*Magnolia* bark, present in the intestinal tea, is highly effective against digestive and intestinal problems. It possesses 1000 times more powerful antioxidant properties than vitamin E. It also controls the body's primary stress hormone, cortisol. By controlling cortisol it cannot only be used as a general anti-stress and anti-anxiety agent, but can also help with a myriad of health issues associated with elevated cortisol, including obesity and diabetes. *Magnolia* bark comprises about 14 weight percent of the intestinal tea.

*Senna* leaf, present in the intestinal tea, has laxative properties, as well as anti-bacterial properties, purging stagnation and accumulation. *Senna* leaf comprises about 11 weight percent of the intestinal tea.

Exude from *aloe* leaves, present in the intestinal tea, are used as a strong purgative and stimulant laxative. *Aloe* also decreases cholesterol and triglycerides, and reduced fasting blood-sugar dramatically due to the stimulating effect if has on the pancreas to produce more insulin. *Aloe* comprises about 11 weight percent of the intestinal tea.

*Prunus,* present in the intestinal tea, is used to help relax and moisten the bowels. *Prunus* promotes bowel movement. *Prunus* comprises about 11 weight percent of the intestinal tea.

Bitter orange, present in the intestinal tea, is popular in many parts of the world for its digestive aide and sleep-assisting properties. This herb assists with pain in the abdomen and regulates constipation and diarrhea. Bitter orange also helps with weight loss and weight management, as it is known to raise metabolism, increase expenditure of calories, improve stamina and energy, and speed up the elimination of unwanted stored fat and suppress the appetite. Bitter orange, present in the intestinal tea, comprises about 11 weight percent of the intestinal tea.

Rhubarb, present in the intestinal tea, is used as a laxative to evacuate the bowels and improve the digestive tract. Rhubarb has also been found useful in treating jaundice and indigestion. Rhubarb has the ability to fight infectious fungi such as *candida*. Rhubarb comprises about 11 weight percent of the intestinal tea.

Licorice, present in the intestinal tea, is a moist, soothing herb that is anti-inflammatory and has laxative effects. It is also used to relax muscles to relieve pain and reduce side effects of many herbs. Licorice comprises about 9 weight percent of the intestinal tea.

The detoxifying herbal tea formulation is useful in clearing heat, cleaning toxins, and creating free flow of energy. The detoxifying tea formulation comprises *cyperus*, Chinese *angelica, trichosanthes,* honeysuckle, *forsythia,* burdock fruit, and dandelion. Six grams of the detoxifying herbal tea are to be mixed in about 8 ounces of hot water and taken orally two times a day in between meals for a determined number of consecutive days. The recited ingredients are well-known medicinal Chinese herbs.

*Cyperus,* present in the detoxifying tea, soothes the liver and is a primary herb for the treatment of irregular menstruation and dysmenorrheal. *Cyperus* comprises about 14 weight percent of the detoxifying tea.

Chinese *angelica,* present in the detoxifying tea, is one of the most commonly used herbs in Chinese medicine. It balances the body's production of estrogen, boosts white blood cells which helps fight inflammation, increases red blood cells, improves liver and kidney function and also keeps the smooth muscles of the arteries dilated, helping to maintain regular blood flow and heart beat. Chinese *angelica* comprises about 11 weight percent of the detoxifying tea.

*Trichosanthes,* present in the detoxifying tea, is a natural antibiotic, expectorant and laxative. It can disperse phlegm, remove pus, expel toxic matter and is anti-inflammatory. It creates a cooling effect in the body. It also helps stimulate the production of body fluids and is used in modern Chinese treatments for diabetes. *Trichosanthes* comprises about 11 weight percent of the detoxifying tea.

Honeysuckle, present in the detoxifying tea, is used to clear heat and remove toxins. Generally, honeysuckle flower has been employed to treat a variety of conditions ranging from fevers, ulcers, inflammation and sore throats to skin infections and releasing poisons from the body. It has also been used for its antiviral properties and to lower blood pressure. Honeysuckle comprises about 11 weight percent of the detoxifying tea.

*Forsythia,* present in the detoxifying tea, is typically used to detoxify the body. It is also often used for the common cold, influenza, allergies and as an antiviral, antibacterial, anti-inflammatory, antipyretic, antiallergenic and as an antioxidant. *Forsythia* comprises about 11 weight percent of the detoxifying tea.

Burdock fruit, present in the detoxifying tea, relieves toxicity and relieves swelling. It has historically been used to treat a wide variety of ailments including arthritis and hair loss but more recently it has been used for bacterial infections, cancer, HIV, kidney stones and to lower blood sugar, helping in the treatment of diabetes. Burdock fruit comprises about 11 weight percent of the detoxifying tea.

Dandelion, present in the detoxifying tea, is a bitter-sweet, cooling herb that has diuretic and laxative effects. It also stimulates liver function, improves digestion and reduces swelling and inflammation. It is used for gall bladder and liver disorders including cirrhosis and jaundice. Dandelion comprises about 11 weight percent of the detoxifying tea.

*Gardenia,* present in the detoxifying tea, one of its main functions is to clear heat. It is traditionally used in Chinese medicine to treat the symptoms of type 2 diabetes and does indeed contain a chemical that reverses some of the pancreatic dysfunctions that underlie the disease. It also has mild antiseptic properties. *Gardenia* comprises about 11 weight percent of the detoxifying tea.

*Coptis,* present in the detoxifying tea, has strong antibiotic properties. It clears heat and cleans toxins, and is commonly used for strep throat urinary tract infections and other infections. *Coptis* comprises about 7 weight percent of the detoxifying tea.

The phytonutrient compounds in Mustard seed, present in the detoxifying tea, protect against gastrointestinal cancer and have anti-inflammatory effects. Additionally, it is antibacterial, antifungal and antiseptic. Mustard seed comprises about 4 weight percent of the detoxifying tea.

The tonifying herbal tea formulation is useful in tonifying and nourishing the body and in slowing the aging process. The tonifying tea formulation comprises goji berries, red reishi mushroom, *rehmannia, polygonum, astragalus,* ginseng, *codonopsis,* and *schizandra.* Ten grams of the tonifying herbal tea are to be mixed in about 8 ounces of hot water and taken orally right before lunch for a determined number of consecutive days. The recited ingredients are well-known medicinal Chinese herbs.

Goji berries, present in the tonifying tea, are reported to contain 18 amino acids (six times higher than bee pollen), more beta carotene than carrots, more iron than spinach, and 21 trace minerals. They also contain vitamin B1, B2, and B6. Goji berries are 13% protein and are extremely high in antioxidants. They have been renowned as one of the most powerful anti-aging foods. They are also helpful against cancer, diabetes, and heart disease, while being beneficial to the liver, immune system and even brain health. Goji berries comprise about 23 weight percent of the tonifying tea.

Red reishi, present in the tonifying tea, known as the "miracle mushroom", has been part of traditional Chinese medicine for more than 2000 years and is widely regarded as the "elixir of life." Used in many tonic formulas, it inhibits tumors, enhances the immune system, tonifies the heart, is anti-inflammatory, increases oxygen absorption, reduces high cholesterol, reduces high blood pressure and is antiviral. It has also been said to treat nervousness and weakness. It has anti-aging properties and promotes longevity. Red reishi comprises about 17 weight percent of the tonifying tea.

The root of prepared rehmannia, present in the tonifying tea, is used medicinally to replenish vitality, to strengthen the liver, kidney and heart. Its astringent compounds halt bleeding of ulcers and reduce inflammation of the digestive system. Other compounds in this herb work to reduce capillary fragility and support liver and adrenal glands. Rehmannia comprises about 14 weight percent of the tonifying tea.

*Polygonum,* present in the tonifying tea, is one of the premier Chinese longevity herbs. By tonifying kidney essence, this herb prevents premature aging, strengthens sperm and ova, maintains the youthful condition and color of hair and also increases sexual vigor. *Polygonum* is also an immune booster and lowers cholesterol and blood pressure. *Polygonum* comprises about 11 weight percent of the tonifying tea.

*Astragalus,* present in the tonifying tea, strengthens vitality and improves the ability to cope with physical and emotional stress. It improves the immune system and the adrenal gland and digestive function. It strengthens and boosts the immune system by improving the ability of macrophages (a type of white blood cells) to fight and devour bacteria, fungi and viruses and is also thought to promote the production of interferon in the body. *Astragalus* makes some cancer medication more effective, thereby allowing less toxic dosages to be used in treatment. *Astragalus* comprises about 11 weight percent of the tonifying tea.

Ginseng, present in the tonifying tea, stimulates and relaxes the nervous system and encourages the secretion of hormones, improves stamina, lowers blood sugar as well as cholesterol levels and increases resistance to disease. In Chinese medicine it is used to quickly restore homeostasis (balance) reducing the effect of aging and enhance physical, sexual and mental performance. Ginseng has excellent antioxidant and anti-fatigue effects. Ginseng comprises about 3 weight percent of the tonifying tea.

*Codonopsis,* present in the tonifying tea, is a safe whole body tonic that has been used in Chinese medicine for centuries to regulate appetite, strengthen the immune system, nourish the lungs, and aid digestion. It is classified as a stomachic, which means that it strengthens the stomach to improve digestive functions. Modern research indicates its ability to lower blood pressure as well as increase red and white blood cells and antibodies. *Codonopsis* is an adaptogen, meaning that it enhances and regulates the body's ability to withstand stress by increasing the body's general performance in ways that help the whole body resist disease. *Codonopsis* benefits the entire body by boosting strength, increasing stamina and alertness, improving memory, rejuvenating the body, and aiding recovery from chronic illness. *Codonopsis* comprises about 9 weight percent of the tonifying tea.

*Schizandra,* present in the tonifying tea, is a potent adaptogenic herb which balances body functions and normalizes the body systems. It optimizes energy during time of stress. It stimulates the immune system and shields against infection. *Schizandra* energizes RNA-DNA molecules to rebuild cells and produce energy. *Schizandra* comprises about 11 weight percent of the tonifying tea.

The relaxing herbal tea formulation is useful in calming, relaxing, and aiding restful sleep. The relaxing tea formulation comprises ginger, lily bulbs, *mimosa* tree bark, *acorus,* sour jujube seeds, yuan zhi, and mint. Seven grams of the relaxing herbal tea are to be mixed in about 8 ounces of hot water and taken orally right before bed for a determined number of consecutive days. The recited ingredients are well-known medicinal Chinese herbs.

Ginger, present in the relaxing tea, relaxes spasms and relieves pain. Ginger also increases circulation and calms and warms internal organs. It also has a descending nature, quelling nausea and vomiting. Ginger comprises about 18 weight percent of the relaxing tea.

Lily bulbs, present in the relaxing tea, treat insomnia and heart palpitations. Its tonic properties make it a good herb for promoting restful sleep and treating restlessness and irritability. Lily bulbs comprises about 14 weight percent of the relaxing tea.

*Mimosa* tree bark, present in the relaxing tea, commonly referred to as "joy bark" or "happy bark" is categorized as a calming spirit herb because it anchors the spirit. It has been used for the treatment of insomnia, as well as depression, melancholy, stress and anxiety. It enhances all aspects of neurotransmitter secretion and regulation in the brain. *Mimosa* tree bark comprises 14 weight percent of the relaxing tea.

*Acorus,* present in the relaxing tea, is one of the most commonly used Chinese herbs for the treatment of mental disorders. It is a general sedative as it tranquilizes the mind and central nervous system. *Acorus* based medications can be used in treating withdrawal symptoms in drug addicts and is also used in the treatment of seizure disorders. It is a great herb to help sleep disorders. Acorns comprises about 14 weight percent of the relaxing tea.

Sour jujube seeds, present in the relaxing tea, are used to treat insomnia, palpitations, anxiety, sweating problems, and poor memory problems. Sour jujube seeds is a natural, safe, nourishing sedative. In Chinese medicine this herb nourishes the two organs responsible for sleep—liver and heart. When balance is brought back to these organs then sleep is done naturally. It also helps with anxiety, overworked mind, restlessness, irritability, night sweats, palpitations and fidgeting. Sour jujube seeds comprise about 14 weight percent of the relaxing tea.

Yuan zhi, present in the relaxing tea, literally translated as "far will" is considered a powerful tonic herb that can help develop the mind and aid in creative thinking. It benefits the mental state including amnesia, anxiety, constrained emotions, dream-disturbed sleep, excessive brooding, fear, forgetfulness or poor memory, insomnia, mental disorientation or confusion, neurasthenia, palpitations, epilepsy, convulsions, pent-up emotional states, irritability and restlessness. Yuan zhi comprises about 14 weight percent of the relaxing tea.

Mint, present in the relaxing tea, clears the head and eyes, dissipates heat, soothes digestions, and soothes the liver. It is also taken to calm the nervous system and as a mild sedative. It eases and unblocks the breathing and respiratory passages and airways. Mint comprises about 10 weight percent of the relaxing tea.

The herbal cleanse formulation is to be taken in a specific protocol in conjunction with a vegan alkalinizing diet By transforming nutrition into an alkalizing pH diet, every cell in the body will be recreated and regenerated. An alkaline diet helps to boost energy levels, improve skin, reduce allergies and enhance mental clarity. Furthermore, once pH balance is achieved, the body instinctively drops to its ideal healthy weight. As soon as the acidic environment is eliminated, there is no need for new fat cells to form, and the remaining fat in your body is no longer needed to store acid wastes, and therefore simply melts away. An alkaline way of life will restore good health that you can see and feel.

Incorporating Kundalini yoga practiced under the supervision of a facilitator as part of the cleanse will balance the body, mind and spirit. Kundalini is different from what most people think of as yoga in America today. It is not a workout, but an ancient technology of angles and vocal vibrations that innervate water and cells in your body to alter your state of consciousness to feel the Divine within you, or to alter your consciousness into another dimension where deep, deep healing can take place. Kundalini yoga is a physical, mental and spiritual discipline for developing and tapping into inner energy and awareness. It incorporates chanting, physical postures and meditation to heal physically, mentally, and spiritually. Kundalini yoga is considered the yoga of awareness because it directly affects human consciousness, develops intuition, increases self knowledge, and unleashes the unlimited creative potential that exists within every human being. Like many other yoga forms, it develops the nervous system, glands and mental control, but is also associated with releasing kundalini energy through asana based exercise and meditation at a safe, rapid, and regulated rate.

Kundalini yoga is part of the cleanse protocol and is practiced under the supervision of a facilitator during the determined number of days of the cleanse at specified times throughout the day to be delineated by the facilitator.

The invention is more easily comprehended by reference to the specific embodiments recited hereinabove which are representative of the invention. It must be understood, however, that the specific embodiments are provided only for the purpose of illustration, and that the invention may be practiced otherwise than as specifically illustrated without departing from its spirit and scope.

What is claimed is:

1. A kit for herbal cleansing comprising five different herbal teas:
   A): a parasite tea comprising *areca* seed, black plum, Sichuan pepper, and daikon radish;
   B): an intestinal tea comprising mountain hawthorn berry, *magnolia* bark, *senna* leaf, *aloe*, *prunus*, bitter orange, rhubarb, and licorice;
   C): a detoxifying tea comprising *cyperus*, Chinese angelica, *trichosanthes*, honeysuckle, *forsythia*, burdock fruit, dandelion, *gardenia*, *coptis*, and mustard seed;
   D): a tonifying tea comprising goji berries, red reishi, *rehmannia, polygonum, astragalus*, ginseng, *codonopsis*, and *schizandra*; and
   E): a relaxing tea comprising ginger, lily bulbs, *mimosa* tree bark, acorus, sour jujube seeds, yuan zhi, and mint.

2. The kit according to claim 1, wherein the tea formulations are dispensed as granules in about 8 ounces of hot water to be taken orally.

3. The kit according to claim 1, wherein the concentration of *areca* seed comprises about 43 weight percent of the parasite tea.

4. The kit according to claim 1, wherein the concentration of black plum comprises about 21 weight percent of the parasite tea.

5. The kit according to claim 1, wherein the concentration of sichuan pepper comprises about 21 weight percent of the parasite tea.

6. The kit according to claim 1, wherein the concentration of daikon radish comprises about 14 weight percent of the parasite tea.

7. The kit according to claim 1, wherein the concentration of mountain hawthorn berry comprises about 20 weight percent of the intestinal tea.

8. The kit according to claim 1, wherein the concentration of *magnolia* bark comprises about 14 weight percent of the intestinal tea.

9. The kit according to claim 1, wherein the concentration of *senna* leaf comprises about 11 weight percent of the intestinal tea.

10. The kit according to claim 1, wherein the concentration of *aloe* comprises about 11 weight percent of the intestinal tea.

11. The kit according to claim 1, wherein the concentration of *prunus* comprises about 11 weight percent of the intestinal tea.

12. The kit according to claim 1, wherein the concentration of bitter orange comprises about 11 weight percent of the intestinal tea.

13. The kit according to claim 1, wherein the concentration of rhubarb comprises about 11 weight percent of the intestinal tea.

14. The kit according to claim 1, wherein the concentration of licorice comprises about 9 weight percent of the intestinal tea.

15. The kit according to claim 1, wherein the concentration of *cyperus* comprises about 14 weight percent of the detoxifying tea.

16. The kit according to claim 1, wherein the concentration of chinese *angelica* comprises about 11 weight percent of the detoxifying tea.

17. The kit according to claim 1, wherein the concentration of *trichosanthes* comprises about 11 weight percent of the detoxifying tea.

18. The kit according to claim 1, wherein the concentration of honeysuckle comprises about 11 weight percent of the detoxifying tea.

19. The kit according to claim 1, wherein the concentration of *forsythia* comprises about 11 weight percent of the detoxifying tea.

20. The kit according to claim 1, wherein the concentration of burdock fruit comprises about 11 weight percent of the detoxifying tea.

21. The kit according to claim 1, wherein the concentration of dandelion comprises about 11 weight percent of the detoxifying tea.

22. The kit according to claim 1, wherein the concentration of *gardenia* comprises about 11 weight percent of the detoxifying tea.

23. The kit according to claim 1, wherein the concentration of *coptis* comprises about 7 weight percent of the detoxifying tea.

24. The kit according to claim 1, wherein the concentration of mustard seed comprises about 4 weight percent of the detoxifying tea.

25. The kit according to claim 1, wherein the concentration of goji berries comprises about 23 weight percent of the tonifying tea.

26. The kit according to claim 1, wherein the concentration of red reishi comprises about 17 weight percent of the tonifying tea.

27. The kit according to claim 1, wherein the concentration of *rehmannia* comprises about 14 weight percent of the tonifying tea.

28. The kit according to claim 1, wherein the concentration of *polygonum* comprises about 11 weight percent of the tonifying tea.

29. The kit according to claim 1, wherein the concentration of *astragalus* comprises about 11 weight percent of the tonifying tea.

30. The kit according to claim 1, wherein the concentration of ginseng comprises about 3 weight percent of the tonifying tea.

31. The kit according to claim 1, wherein the concentration of *codonopsis* comprises about 9 weight percent of the tonifying tea.

32. The kit according to claim 1, wherein the concentration of *schizandra* comprises about 11 weight percent of the tonifying tea.

33. The kit according to claim 1, wherein the concentration of ginger comprises about 18 weight percent of the relaxing tea.

34. The kit according to claim 1, wherein the concentration of lily bulbs comprises about 14 weight percent of the relaxing tea.

35. The kit according to claim 1, wherein the concentration of *mimosa* tree bark comprises about 14 weight percent of the relaxing tea.

36. The kit according to claim 1, wherein the concentration of acorus comprises about 14 weight percent of the relaxing tea.

37. The kit according to claim 1, wherein the concentration of sour jujube seeds comprises about 14 weight percent of the relaxing tea.

38. The kit according to claim 1, wherein the concentration of yuan zhi comprises about 14 weight percent of the relaxing tea.

39. The kit according to claim 1, wherein the concentration of mint comprises about 10 weight percent of the relaxing tea.

40. An herbal cleanse formulation, A kit for herbal cleansing comprising five different herbal teas:
- A): a parasite tea comprising about 43 weight percent *areca* seed, about 21 weight percent black plum, about 21 weight percent Sichuan pepper, and about 14 weight percent daikon radish;
- B): an intestinal tea comprising about 20 weight percent mountain hawthorn berry, about 14 weight percent *magnolia* bark, about 11 weight percent *senna* leaf, about 11 weight percent *aloe*, about 11 weight percent prunus, about 11 weight percent bitter orange, about 11 weight percent rhubarb, and about 9 weight percent licorice;
- C): a detoxifying tea comprising about 14 weight percent *cyperus*, about 11 weight percent Chinese *angelica*, about 11 weight percent *trichosanthes*, about 11 weight percent honeysuckle, about 11 weight percent *forsythia*, about 11 weight percent burdock fruit, about 11 weight percent dandelion, about 11 weight percent *gardenia*, about 7 weight percent *coptis*, and about 4 weight percent mustard seed;
- D): a tonifying tea comprising about 23 weight percent goji berries, about 17 weight percent red reishi, about 14 weight percent rehmannia, about 11 weight percent polygonum, about 11 weight percent astragalus, about 3 weight percent ginseng, about 9 weight percent *codonopsis*, and about 11 weight percent *schizandra*; and
- E): a relaxing tea comprising about 18 weight percent ginger, about 14 weight percent lily bulbs, about 14 weight percent *mimosa* tree bark, about 14 weight percent acorus, about 14 weight percent sour jujube seeds, about 14 weight percent yuan zhi, and about 10 weight percent mint.

* * * * *